(12) United States Patent
Marrongelle et al.

(10) Patent No.: US 6,517,832 B1
(45) Date of Patent: Feb. 11, 2003

(54) FORMULATIONS AND METHODS FOR TREATING CHRONIC MIGRAINE

(76) Inventors: Jeffrey L. Marrongelle, 1629 Long Run Rd., Orwigsburg, PA (US) 17972; Thomas J. Staverosky, 1537 Mineral Springs Rd., Reading, PA (US) 19602

( * ) Notice: Subject to any disclaimer, the term of this patent is extended or adjusted under 35 U.S.C. 154(b) by 0 days.

(21) Appl. No.: 09/935,945

(22) Filed: Aug. 24, 2001

(51) Int. Cl.⁷ .................. A01N 63/00; A01N 65/00; A61K 9/48; C12N 1/20
(52) U.S. Cl. .............. 424/93.45; 424/93.4; 424/93.48; 424/452; 424/465; 424/725; 435/252.9; 435/822
(58) Field of Search .............. 435/243; 424/93.4, 424/465, 452

(56) References Cited

U.S. PATENT DOCUMENTS

| | | | |
|---|---|---|---|
| 5,589,168 A | * 12/1996 | Allen et al. | 424/93.4 |
| 5,939,076 A | * 8/1999 | Allocca | 424/400 |
| 6,113,907 A | * 9/2000 | Khwaja et al. | 424/730 |
| 6,132,724 A | * 10/2000 | Blum | 424/725 |
| 6,297,273 B1 | * 10/2001 | Romanczyk | 514/456 |

* cited by examiner

*Primary Examiner*—David M. Naff
*Assistant Examiner*—Deborah K. Ware
(74) *Attorney, Agent, or Firm*—A. R. Eglington

(57) ABSTRACT

A prophylactic treatment for the human malady clinically described as migraine headache comprising daily administration in unit dosage form of a first formulation which comprises a major amount of bioactive peptides and a minor amount of probiotics. Concurrently, daily administration in dosage form of a second formulation of a major amount of active components like malic acid, sylibum marianum, acetyl-L-cysteine, copper chelate, zinc gluconate, aspartate and bromelain. A minor amount of plant derivatives excipients comprise the balance of the second formulation. Preferably, these plant derivatives include beet root, powder, watercress, celery, dandelion, capsicum and artichoke extract.

8 Claims, 1 Drawing Sheet

Figure 1. Results of Migraine Specific Quality of Life Questionnaire
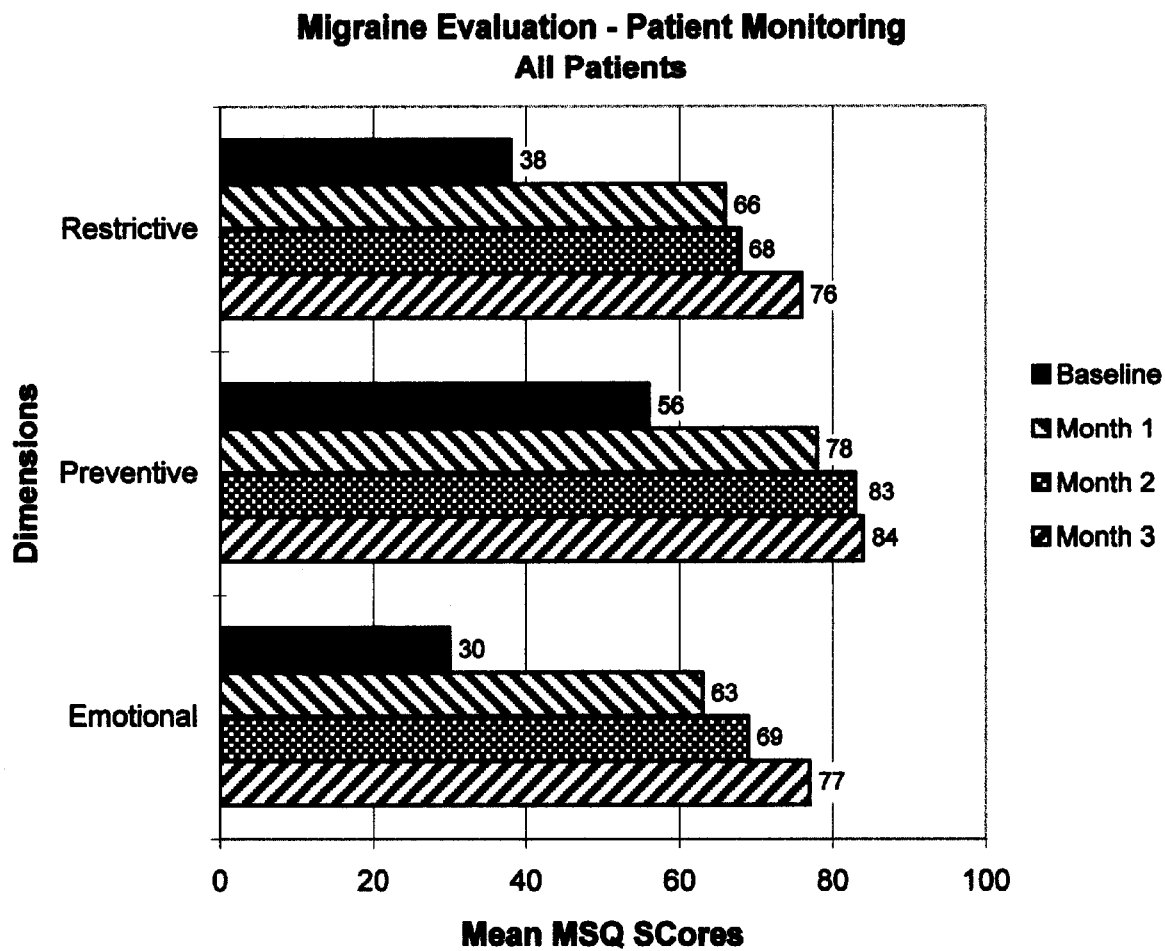
0 → 100 is a quality of life scale with 0 the lowest and 100 the highest
MSQ = Migraine specific quality of life questionnaire

FORMULATIONS AND METHODS FOR TREATING CHRONIC MIGRAINE

CROSS REFERENCE TO OTHER APPLICATIONS

This is a non-provisional patent specification and claims submitted for an official filing receipt under Patent Code 111(a).

BACKGROUND OF THE INVENTION

Headaches range from the rare and excruciating type, known as clusters, through the common tension-type (stress-induced), to the somewhat less common, but notorious, migraine, with or without an aura effect. Migraines have been attributed to blood vessels in the brain being constricted and then relaxing, thus altering blood flow. It was thought early on that the pain of migraine was of vascular origin and caused by excessive dilation of branches of the common carotid artery bed. Currently, researchers are zeroing in on the trigeminal nerve system, and the nerve chemical Serotonin, in particular, as one set of candidate headache pain culprits.

While significant advances have been made in dealing with the pain of migraine, little has had a dramatic effect in preventing the next attack or curing the disease. Indeed, the dominant medical community generally describes migraine as an incurable disease of unknown cause. Many migraine sufferers have reached a level of total frustration due to the lack of help they receive from the dominate or alternative medical community. Most have visited multiple health care professionals and have tried numerous prescription, over the ouncter, and natural products in an attempt to find a solution.

Consequently, a variety of vaso-constrictor agents have been promoted to alleviate this type of headache. Such compounds were tested (or shown) to constrict the carotid artery bed of an anesthetized dog. A medically accepted treatment include use of the a complex heterocyclic compound of the substituted indoles. Sumatriptan succinate (IMITREX, Glaxo Group) is an example of such a complex organic compound that activates the chemical messengers which cause blood vessels in the brain to constrict, thus lessening the pain effects of a migraine. Compare U.S. Pat. No. 4,816,470 of Mar. 28, 1989 to Dowle et al, and U.S. Pat. No. 5,037,845, of Aug. 6, 1991 to Oxford. The current Physician's Desk Reference denotes a plethora of side effects with sumatriptan migraine therapy. Indeed, the FDA-approved labeling for IMITREX declares it is not effective for other types of head pain, and because of the risk of known side affects, that IMITREX is generally used when other treatments prove ineffective.

There have not been corresponding advances in the area of migraine preventatives. While there are a variety of preventative pharmaceutical approaches available, none has proven to be broadly effective for an extended time frame. Again, the side effects associated with the various options limits their value. It is also fairly common for preventative approaches to work for limited amounts of time. Indeed, we will be interested to follow our study group to document their condition six and twelve months down the road to see if the improvement they have experienced lasts.

Whatever the neurological pathway to migraine relief, less complex methods are desired, in using pharmacologically benign compositions, in formulations that are desirable alternatives to potent organic compositions like sumatriptan. The search for formulations and methods that are substantially devoid of the clinically-established side effects seen with complex organic compounds, are in order. Morever, formulations based on natural substances that are of low cost seem an economic imperative for those chronic migraine victims of more modest financial means.

The approach utilized in this study is based on a new theory as to the cause of migraine. We believe that migraine is the deterioration of normal function. We believe that this deterioration of normal function is in one of two areas; either the body is not getting what it needs (digestion), or the body is unable to remove waste and toxins from the body (elimination). By focusing our attention and efforts on returning the digestive function to normal and assisting the liver, kidneys, and spleen with targeted nutritional support, we believe that the manifestation of migraine will diminish or disappear in most sufferers. At the very least, we believe we can document a significant improvement in the quality of life for most migraineurs.

OBJECTS OF THE INVENTION

It is a principal object of the present invention to provide an economical alternative to costly prescription remedies for the prophylactic treatment of the condition often clinically described as migraine headache.

It is another object of the invention to provide an orally administerable formulation composed of low cost and benign natural substances, such as among those that have already been demonstrated as being beneficial and nutritional substances, that have been clinically shown to relieve refractory migraine.

Still another object of the invention is to provide a formulation that provides macro and micro nutrients that are conducive to good health while providing for the prophylactic treatment of migraine.

Yet another object of the invention is to provide formulations that lack the side affects liability of complex neuroleptic agents, like the substituted indoles, now serving as a prescription treatment of migraine.

SUMMARY OF THE INVENTION

According to the invention, there is provided a method of treating a human being suffering from the pain resulting from headache, migraine headache, and cluster headache by administering a pharmaceutically acceptable composition, comprising a number of selected active ingredients in an effective amount. Such a formulation of several discrete compounds is set out in Example I, together with one or more pharmacologically acceptable carriers or excipients. These prophylactic formulations are taken orally via gelatin capsules, usually being ingested on a daily basis.

In current usage of the two already established formulations comprising natural substances serving as a prophylactic regimen, has been seen to afford relief from migraine.

DETAILED DESCRIPTION OF A PREFERRED EMBODIMENT

Accordingly, the inventive methods provides for concurrent administration of two discrete formulations of known beneficial substances, the first formulation is a blend of select ingredients and is thought to improve digestion in most patients.

Formulation I is a unique blend of two ingredients in a gelatin capsule, which blend primarily serves to focus on returning the digestive system to normal function. The first composition of Formulation I is a fish protein concentrate of bioactive peptide. The second composition of the group are probiotics, which are known to be beneficial bacteria, that normally inhabit a mammalian digestive (intestinal) tract, such as the acidophilus microorganism found in yogurt. It is an important agent, shown to be effective in absorbing toxins from both the small intestine and the bowel. This two part formulation is assembled in the weight ratios set out in Working Example I, as in Foundation Formula of The Forever Well entity, Reading, Pa.

The second formulation (II) is a combination of as many as 21 substances, all known to be both benign and beneficial, included selected vitamins, trace minerals, herbs, micronutrients, and macronutrients (Renew Formula®, of the Foreverwell entity). They are assembled in the weight ratios set out in Working Example II. They are well adapted to using standard gelatin capsules as the unit dosage form.

Of the vitamins, included are vitamin B complex species, like B1, B6, and inositol (cis-1,2,3,5-trans, 4, 6, cyclohexanehexol). The trace minerals include magnesium as the aspartate, copper as a chelate, manganese as glycerolphosphate, and zinc as the gluconate. Herbs include silybum marianum (milk thistle), beet root powder, watercress, celery, dandelion, parsley, and capsicum. Micronutrients are malic acid, proanthocyanidins, N-Acetyl-L-Cysteine, and SOD (superoxide dismutase). The macronutrients include pyridoxal-5 phosphate, and Agaricus Blazei.

Pharmaceutically acceptable formulations for oral administration may take the form of, for example, tablets or capsules prepared by conventional means, with acceptable excipients, such as binding agents, for example, maize starch, or hydroxymethyl cellulose; fillers, for example, lactose, sucrose, mennitol, and maize starch; lubricants, for example, stearic acid, polyethylene glycol, magnesium stearate, metallic or silica, disintegrants, for example, potato starch, or wetting agents, e.g., sodium lauryl sulfate. The tablets may be coated by methods well known in the arts.

Liquid preparations for oral administration may take the form of, for example, aqueous or oily solutions, syrups, elixirs, emulsions or suspensions, or they may be presented as a dry product for reconstitution with water or other suitable vehicle before use. Such liquid preparations may be prepared by conventional means, with pharmaceutically acceptable additives, such as suspending agents, for example, sorbitol syrup, glucose-sugar syrup, or gelatin; emulsifying agents such as lecithin, acacia, or sorbitan mon-oleate; non-aqueous vehicles like oily esters, or ethyl alcohol; and preservatives like methyl or propel p-hydroxy benzoates, or sorbic acid. Such liquid preparations may also contain conventional buffers, flavoring, coloring, and sweetening agents, as appropriate. The prophylactic effects for relief of migraine are effected by taking three capsules (500 mg each) of Formulation I, along with two capsules of Formulation II (400 mg each) before each of the two largest meals of the day, on a daily basis, longer term for an adult in the weight range of 125–200 lb. To limit initial digestive disturbances, take a reduced regimen for the first week. For the initial regime, the reduced dosage of the two capsules is 1400 mg daily.

A proposed dose of the compounds of the invention for oral administration to a human (about 160 lb.) body weight, for the treatment of migraine, is 2300–4600 mg of capsule daily of the ingredients, which dose could be administered up to eight times per day, but more usually one to four times a day, in divided dosages, as noted. It should be understood that unless otherwise indicated, the dosages are referred to in terms of the weight of the active components of the two formulations.

| WORKING EXAMPLE I - FOUNDATION FORMULA ® | |
|---|---|
| COMPOSITION | AMOUNT PER CAPSULE |
| Bioactive peptides | 375 mg |
| Probiotics | 62.5 mg |

Bioactive peptides which as are available in a particular predigested fish protein concentrate are sold under the trade name Seacure and made available by Proper Nutrition, Inc., Reading, Pa.

Probiotics such as are made available in various strains and custom blends by Nebraska Cultures and other providers. These beneficial intestinal bacteria assist in the digestion and absorption of food. the selected blend used in Foreverwell Foundation formula includes the DDS-1 strain of acidophilus, *Lactobacilus bulgaricus, Bifido bacterium,* and *Enterococcus fascium.*

The DDS-1 strain of the acidophilus is described in product sheets and is available from Nebraska Cultures, Walnut Creek, Calif. *L. bulgaricus* is also available from Nebraska Cultures, as is *bifidobacterium bifidum* and *enterococcus faecium.* The last species is also sourced in U.S. Pat. No. 5,589,168, granted Dec. 31, 1996 to Allen et al, titled "PROBIOTIC.".

| WORKING EXAMPLE II - RENEW FORMULA ® | |
|---|---|
| COMPOSITION | AMOUNT PER CAPSULE |
| Malic Acid | 70 mg |
| Silybum marianum | 15 mg |
| N-Acetyl-L-cysteine[1] | 40 mg |
| Copper chelate | 1 mg |
| Zinc gluconate | 5 mg |
| Magnesium aspartate | 10 mg |
| Proanthocyanidins[2] | 10 mg |
| Manganese glycerolphosphate | 1 mg |
| B1 thiamine mononitrate | 5 mg |
| B2 -Riboflavin | 5 mg |
| Inositol (hexahydroxycyclohexane) | 5 mg |
| Beet root powder | 10 mg |
| Watercress | 5 mg |
| Celery | 5 mg |
| Dandelion | 5 mg |
| Capsicum | 5 mg |
| Artichoke Extract | 100 mg |
| SOD (superoxide dismutase)[3] | 250 mcg |
| Pyridoxal 5 Phosphate (B6) | 25 mg |
| Agaricus Blazei | 75 mg |
| Bromelain | 100 mg |
| TOTAL | 498 mg |

[1]Acetyl derivative of L-cysteine, an amino acid. Osilated as the HCl salt preparation per Monograph 2787, Merck Index, Eleventh Ed. (1989).
[2]An analog of cyandin chloride, a substituted benzyopyrylium preparation and properties Monograph 2694, Merck Index, 11th Edition (1989).
[3]Superoxide dismutase extracts of ox erythroctes are disclosed in the scientific literature. French patent application Ser. No. 73.13670, filed April 16, 1973, describes superoxide dismutase extracts from marine bacteria strains, as well as a process for their preparation, which process does not form any part of the present invention.

The other ingredients are readily available from various suppliers of natural supplement components. Proanthocyanidins are an antioxidant component of grape seed. Capsicum is cayenne pepper, and *Agaricus Blazei* is a mushroom. Bromelain is a digestive enzyme derived naturally from pineapple, and which is commercially available from makers of nutritional supplements.

The several components of the Renew Formula (Working Example II) recite the optimal number of elements blended for a unit dosage, such as per capsule. Still, the essential components are malic acid, silybum marianum, the L-cysteine derivative, magnesium aspartate, copper chelate, and zinc gluconate (Cu/Zn ratio of 1:5). The other minor concentration elements are useful adjuncts for optimal effectiveness, but they are not essential to an effective unit dosage. For the Foundation Formula (R), unit dosages, both the bioactive pepides and probiotics are needed for their efficacy.

PROTOCOL FOR DESCRIBED PRODUCT EVALUATION VS. MIGRAINE

Criteria used to select participants were rather broad. Patients could be male or female, at least 18 years of age, and have suffered migraines for at least one year. Due to the relative short term of the evaluation effort (90 days), we selected patients who suffered at least two migraines per month on a consistent basis. Applicants with serious head or neck trauma in their medical histories were eliminated. No consideration relative to inclusion or exclusion from the study was given to the patients' current or previous use of pharmaceutical, over the counter, or natural products.

Patients were provided with detailed descriptions of the products and the specific protocol they were expected to follow. All participants were asked to confirm that they were willing to follow the study protocol for the 90 days of the study. It was also made clear that they had no obligation to remain in the study. If, for any reason they became uncomfortable with the products, they were instructed to simply stop taking the products. All participants confirmed their interest to be part of the product evaluation effort.

As these formulations are normally intended to improve digestive and bowel elimination functions, some users may experience some digestive disturbance (diarrhea) for the first few days. In an effect to limit any discomfort, it is recommended that the following dosage schedule be followed:

Day 1 through Day 3: Take two capsules of Foundation Formula (Formulation I) and one capsule of Renew Formula (Formulation II) five to ten minutes before your main meal of the day;

Day four through Day six: Take two capsules of Foundation Formula and one capsule of Renew Formula five to ten minutes before your two largest meals of the day. At this point, you will be taking four capsules of Foundation Formula and two capsules of Renew Formula.

Day seven through the remainder of the study; take three capsules of Foundation Formula and two capsules of Renew Formula five to ten minutes before your two largest meals of the day. At this point, you will be taking the full recommended dosage, six capsules of Foundation Formula and four capsules of Renew Formula.

The efficacy has been assessed by use of the "Migraine-Specific Quality of Life" questionnaire (M.S.Q. v.2.1), Copyright 1998 by Glaxo-Wellcome Inc., which protocol is distributed by the Medical Outcome Trust of Boston, Mass. 02116 (PMB #5031). Participants completed the MSQ queries at baseline, at 30 days, and again at 60 and 90 days.

The MSW is a 14-item questionnaire that assesses aspects of health believed to be particularly affected by migraine. Three dimensions are measured: role-function restrictive (the degree to which performance of normal activities is restricted or limited by migraine); role function preventive (the degree to which performance of normal activities is presented or interrupted by migraine); and emotional function (the emotional effects of migraine). For example, typical questions address migraine-associated problems in attending social activities (role function restrictive) or the degree to which a migraine patient feels their migraines are a burden for others (emotional function). The MSQ has shown evidence of reliability and validity in migraine suffers participating in clinical trials.

After following the above daily regiment by the taking of the two formulations, for a period of 12 weeks, the MSG. v.2.1 questionnaire was presented to the study of 40 persons. It involves picking one of six listed responses to 14 questions, directed to the impact of migraine incidents on daily living currently given both before starting the regimen, and after the prescribed evaluation period. Patients are asked to provide their responses to each question using a standard a six-point Likert-type scale (None of the time; a little bit of the time; some of the time; a good bit of the time; most of the time; all of the time). MSQ data entered using the MSQ Analyzer are scored automatically. Each MSQ dimension is scored independently from 0 to 100 such that a higher score indicates a better quality of life. The consolidated responses of the study conducted with the formulations of the present invention are set forth below.

The MSQ was completed and mailed to the study administrator at 30-day intervals. Subsequently, the data was inserted into the computer program provided by Medical Outcomes Trust. Data analysis was conducted according to the redesigned software. Each of the three MSQ dimensions was scored separately and transformed onto a scale ranging from 0 (least favorable score) to 100 (most favorable score). Graphical representations of individual data, as well as group data, are presented in FIG. 1.

BRIEF DESCRIPTION OF THE DRAWINGS

FIG. 1 is a bar chart of the study data plotting the parameters of Restrictive-, Preventive-, and Emotional-, each against mean MSQ scores for the baseline values, at one, -two and -three months. The import of these quantitive responses is that for each dimension, the numerical ratings substantially surpass the baseline at one month. They continue to increase appreciably up to the three month's end point of the study.

Patients experienced significant and sustained improvements in quality of life during the 90 days of the study. Although not asked directly on the questionnaire, most participants reported significant reduction in the frequency and duration of their migraine headaches.

Our study participants experienced an improvement in each of the three dimensions of the MSQ. Role Function-Restrictive showed a quality of life increase from a baseline of 38 to a ninety day (90) number of 76. Role Function-Preventive increased from baseline 56 to a ninety (90) day number of 84. Most impressive of all was the increase in quality of life as measured by the Emotional Function dimension where there was a ninety (90) day increase from 30 to 77.

The study clearly indicates that it is possible to significantly improve the quality of life of migraine sufferers with targeted nutritional therapy. Additionally, the fact that the supplements caused no noticeable side effects resulted in a high level of patient satisfaction and compliance.

CONCLUSION

These study results support the theory presented herein that migraines are caused by the deterioration of underlying normal function in the human body. We have shown that by improving the function of the digestive system and the elimination function that the manifestation of migraine diminishes, or ceases. Although the study instrument measures specific quality of life markers, it is critical to note that over 50% of the study participants also report that they are virtually migraine free. This includes participants who have suffered migraine disease for over 25 years and have tried every treatment available, natural and pharmaceutical.

What is claimed is:

1. A first pharmaceutical composition, in unit dosage form which comprises a major percent by weight of bioactive peptides consisting essentially of fish protein concentrate and a minor percent by weight of probiotics selected from the group consisting of DDS-1 strain of *Lactobacillus acidophilus, Lactobacillus bulgaricus, Bifidobacterium bifidum* and *Enterococcus faecium*.

2. A second pharmaceutical composition in unit dosage form which comprises:
   (i) a minor amount by weight percent of pharmaceutically acceptable excipients comprising:
      (a) plant derivatives selected from the group consisting of beet root powder, watercress, celery, dandelion, capsicum, and artichoke extract;
      (b) biochemicals selected from the group consisting of proanthocyanidins, maganese glycerolphosphate, thiamin mononitrate, riboflavin, inositol, and superoxide dismutase; and
      (c) pyridoxal-5 phosphate; and,
   (ii) a major amount of active components consisting essentially of malic acid, Silybum marianum, acetyl L-cysteine, copper chelate, zinc gluconate, magnesium aspartate, and bromelain.

3. A prophylactic method for treating chronic migraine comprising administering on a daily basis to humans a first pharmaceutical composition comprising a major percent by weight of bioactive peptides consisting essentially of fish protein concentrate and a minor percent by weight of probiotics selected from the group consisting DDS-1 strain of *Lactobacillus acidophilus, Lactobacillus bulgaricus, Bifidobacterium bifidum* and *Enterococcus faecium* in a unit dosage amount ranging from 1000 to 3000 mg in a form of delivery selected from the group consisting of capsules, tablets, syrups, and elixirs, and concurrently administering with said first pharmaceutical composition on a daily basis to said humans the second pharmaceutical composition of claim 2 in a unit dosage amount ranging from 400 to 1600 mg in a form of delivery selected from the group consisting of capsules, tablets, syrups, and elixirs.

4. The method of claim 3 wherein the unit dosage amount of the first pharmaceutical composition is provided by capsules each comprising 500 mg of said composition.

5. The method of claim 3 wherein the unit dosage amount is 400 mg said second pharmaceutical composition.

6. The method of claim 3 comprising a dosage regimen of two to six capsules per day to provide said unit dosage amount of said first pharmaceutical composition.

7. The method of claim 6 wherein said dosage regimen is three to six capsules per day.

8. The method of claim 3 comprising a dosage regimen of one to four capsules per day of said second pharmaceutical composition.

* * * * *